US00PP13318P2

(12) United States Plant Patent
Kobayashi

(10) Patent No.: US PP13,318 P2
(45) Date of Patent: Dec. 3, 2002

(54) POINSETTIA PLANT NAMED 'ECKALARIC'

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/968,338

(22) Filed: Sep. 30, 2001

(51) Int. Cl.[7] ..... A01H 5/00
(52) U.S. Cl. ..... Plt./306
(58) Field of Search ..... Plt./306

(56) References Cited

U.S. PATENT DOCUMENTS

PP8,817 P * 7/1994 Fruehwirth ..... Plt./306
PP10,182 P * 1/1998 Zerr ..... Plt./306
PP10,572 P * 8/1998 Fruehwirth ..... Plt./307

OTHER PUBLICATIONS

UPOV ROM GTITM Computer Database, GTI Jouve Retrieval Software 2002/02, Citation(s) for 'Eckalaric'.*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Poinsettia plant named 'Eckalaric', characterized by its large inflorescences with pink-colored flower bracts; dark green-colored leaves; uniform and mounded plant habit; early flowering; and good post-production longevity.

2 Drawing Sheets

BOTANICAL CLASSIFICATION

*Euphorbia pulcherrima.*

BACKGROUND OF THE INVENTION

The present Invention relates to a new and distinct cultivar of Poinsettia plant, botanically known as *Euphorbia pulcherrima* Willd., and hereinafter referred to by the name 'Eckalaric'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia is a naturally-occurring whole plant mutation of a unnamed proprietary induced mutation, not patented, that originated by exposing unrooted cuttings of the *Euphorbia pulcherrima* Willd. cultivar Bright Red Freedom, disclosed in U.S. Plant Pat. No. 10,572, to gamma radiation. The new Poinsettia was discovered and selected by the Inventor as a single plant within a population of plants of the irradiated selection on or about Aug. 19, 1998, in a controlled environment in Encinitas, Calif.

Asexual reproduction of the new Poinsettia by terminal cuttings taken at Encinitas, Calif., since 1998, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckalaric'. These characteristics in combination distinguish 'Eckalaric' as a new and distinct cultivar:

1. Large inflorescences with pink-colored flower bracts.
2. Dark green-colored leaves.
3. Uniform and mounded plant habit.

4. Early flowering, natural season flower maturity date is November 20 for plants grown in Encinitas, Calif.; response time, about 8.5 weeks.
5. Good post-production longevity.

Plants of the new Poinsettia can be compared to plants of the cultivar Bright Red Freedom. In side-by-side comparisons conducted in Encinitas, Calif., plants of the new Poinsettia differed primarily from plants of the cultivar Bright Red Freedom in flower bract color as plants of the cultivar Bright Red Freedom have red-colored flower bracts.

Plants of the new Poinsettia are most similar to plants of the cultivar 490 Pink, disclosed in U.S. Plant Pat. No. 8,817. In side-by-side comparisons conducted in Encinitas, Calif., plants of the new Poinsettia differed primarily from plants of the cultivar 490 Pink in the following characteristics:

1. Plants of the new Poinsettia were larger than plants of the cultivar 490 Pink.
2. Plants of the new Poinsettia had larger inflorescences than plants of the cultivar 490 Pink.
3. Flower bracts of the new Poinsettia were orientated more upright than flower bracts of the cultivar 490 Pink.
4. Flower bracts of the new Poinsettia had smooth surfaces whereas flower bracts of the cultivar 490 Pink had puckered surfaces.
5. Flower bract color of the new Poinsettia was brighter pink than flower bract color of plants of the cultivar 490 Pink.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical flowering plant of 'Eckalaric' grown in a 16.5-cm container.

The photograph at the top of the second sheet comprises a top perspective view of a typical flowering plant of 'Eckalaric'.

The photograph at the bottom of the second sheet is a close-up view of typical leaves and flower bracts of 'Eckalaric' (left) and '490 Pink' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the winter under commercial practice in a polyethylene-covered greenhouse with day temperatures about 24° C., night temperatures about 19° C., and light levels about 4,000 foot-candles. Single plants were grown in 16.5-cm pots and pinched once. Plants were flowered under natural season short day/long night conditions. Plants were about 17 weeks from unrooted cuttings when the photographs and the detailed botanical description were taken.

In the following description, color references are made to The Royal Horticultural Society Colour Chart except where general terms of ordinary dictionary significance are used.

Botanical classification: *Euphorbia pulcherrima* Willd. cultivar Eckalaric.

Parentage: Naturally-occurring whole plant mutation of a unnamed proprietary *Euphorbia pulcherrima* Willd. induced mutation, not patented.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous and freely-branching.

Plant description:

*Plant form.*—Inverted triangle, top of plant rounded and mounding.

*Growth habit.*—Upright and uniform plant habit. Moderate vigor.

*Plant height.*—About 28 cm.

*Plant diameter or spread.*—About 43 cm.

*Lateral branch description.*—Quantity: About eight lateral branches develop after pinching. Length: About 20 cm. Diameter: About 6.5 mm. Internode length: About 2 cm. Color: 146A.

*Foliage description.*—Arrangement: Alternate, single. Quantity of leaves per lateral branch: About eight. Length: About 12 cm. Width: About 9.5 cm. Shape: Mostly elliptic with irregular lobing. Apex: Acuminate. Base: Acute. Margin: Entire with irregular lobing. Venation pattern: Pinnate. Texture: Upper surface: Glabrous. Lower surface: Slightly pubescent. Surface: Mostly flat. Color: Young foliage, upper surface: 147A. Young foliage, lower surface: Darker than 147B. Mature foliage, upper surface: Darker than 147A. Mature foliage, lower surface: 147B. Venation, upper and lower surfaces: 147C. Petiole: Length: About 5.5 cm. Diameter: About 2 mm. Color: 183B.

Inflorescence description:

*Inflorescence type and habit: Inflorescences are compound corymbs of cyathia with colored flower bracts subtending the cyathia. Inflorescences are not fragrant. Inflorescences persistent.*

*Natural flowering season.*—Autumn/winter in Northern Hemisphere. Flower initiation and development is induced under long nyctoperiod conditions. Response time, about 8.5 weeks; natural season flower maturity date is November 20 for plants grown in Encinitas, Calif.

*Post-production longevity.*—Plants of the new Poinsettia maintain good substance and bract color for about three to four weeks under interior conditions.

*Quantity of inflorescences per plant.*—One per lateral branch, about eight.

*Inflorescence size.*—Diameter: About 34 cm. Height (depth): About 3.75 cm.

*Flower bracts.*—Quantity: About 20 bracts per inflorescence. Length, largest bracts: About 13 cm. Width, largest bracts: About 11 cm. Shape: Mostly elliptic with irregular lobing. Apex: Acuminate. Base: Acute. Margin: Entire with irregular lobing. Texture, upper and lower surfaces: Glabrous, velvety. Surface: Flat. Orientation: Horizontal to slightly drooping. Color: Developing or transitional bracts, upper surface: Irregular and random areas of 52A and 147A, then becoming mostly 52A. Developing or transitional bracts, lower surface: Irregular and random areas of 52B and darker than 147B, then becoming mostly 52B. Fully developed bracts, upper surface: 51B; color fading to 51C with subsequent development. Fully developed bracts, lower surface: 51B to 51C. Venation, upper and lower surfaces: Same as ground color. Bract petiole: Length: About 4 cm. Diameter: About 2 mm. Color: 53D.

*Cyathia.*—Quantity: About 9 per corymb. Diameter of cyathia cluster: About 3 by 3.5 cm. Length: About 1 cm. Width: About 5 mm. Shape: Ovoid. Color: Immature: 144B. Mature: 144B to 144C. Peduncle: Length: About 4 mm. Diameter: About 2 mm. Aspect: Strong, erect. Color: 144C. Stamens: Stamen number: About 5 to 10 per cyathium. Anther shape: Oval. Anther length: Less than 1 mm. Anther color: 164C. Amount of pollen: Scarce. Pollen color: 7A. Pistils: None observed. Nectary number: One per cyathia. Nectary color: 23A.

*Disease/pest resistance.*—Resistance to pathogens and pests common to Poinsettias has not been observed on plants grown under commercial conditions.

It is claimed:

1. A new and distinct cultivar of Poinsettia plant named 'Eckalaric', as illustrated and described.

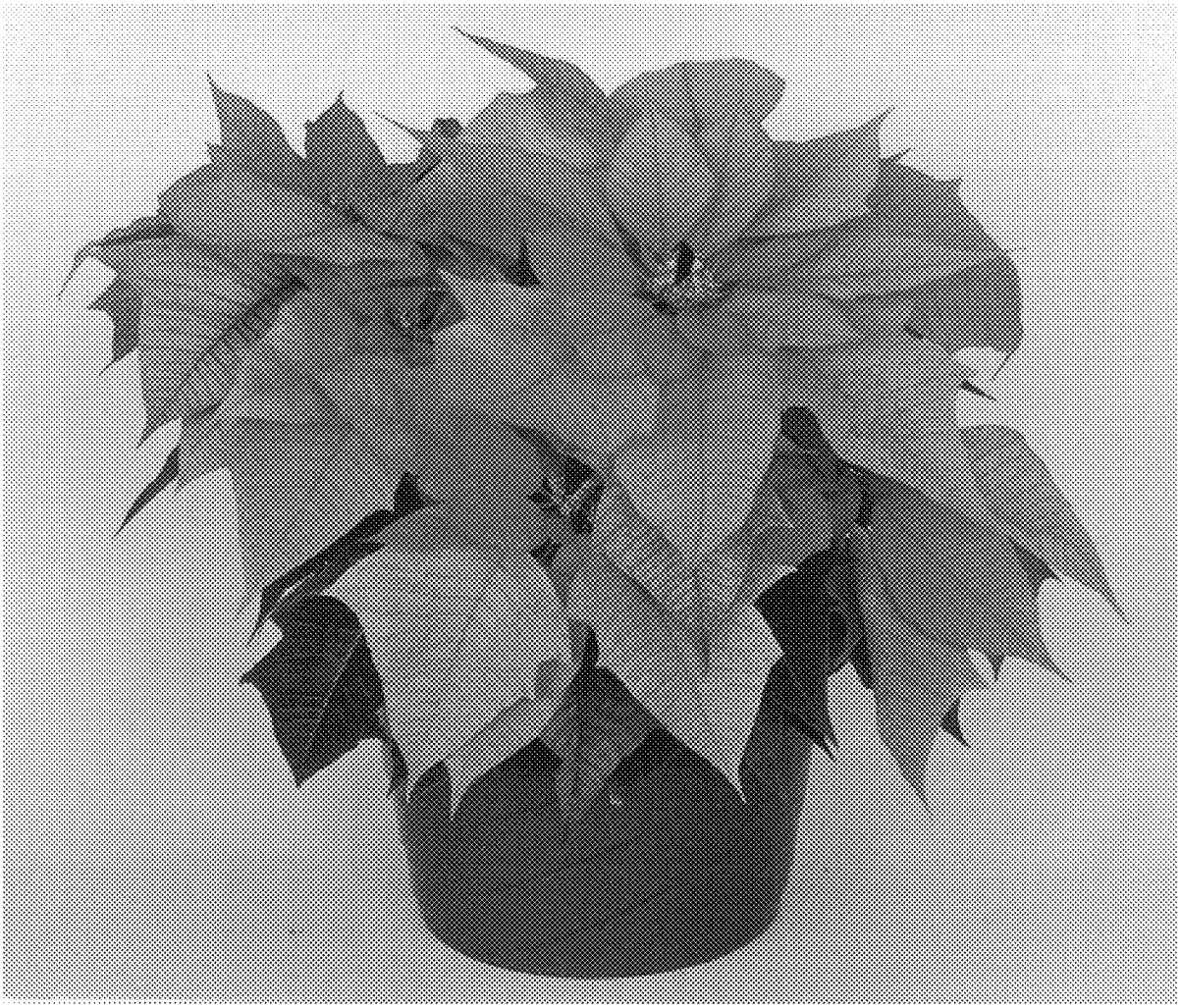

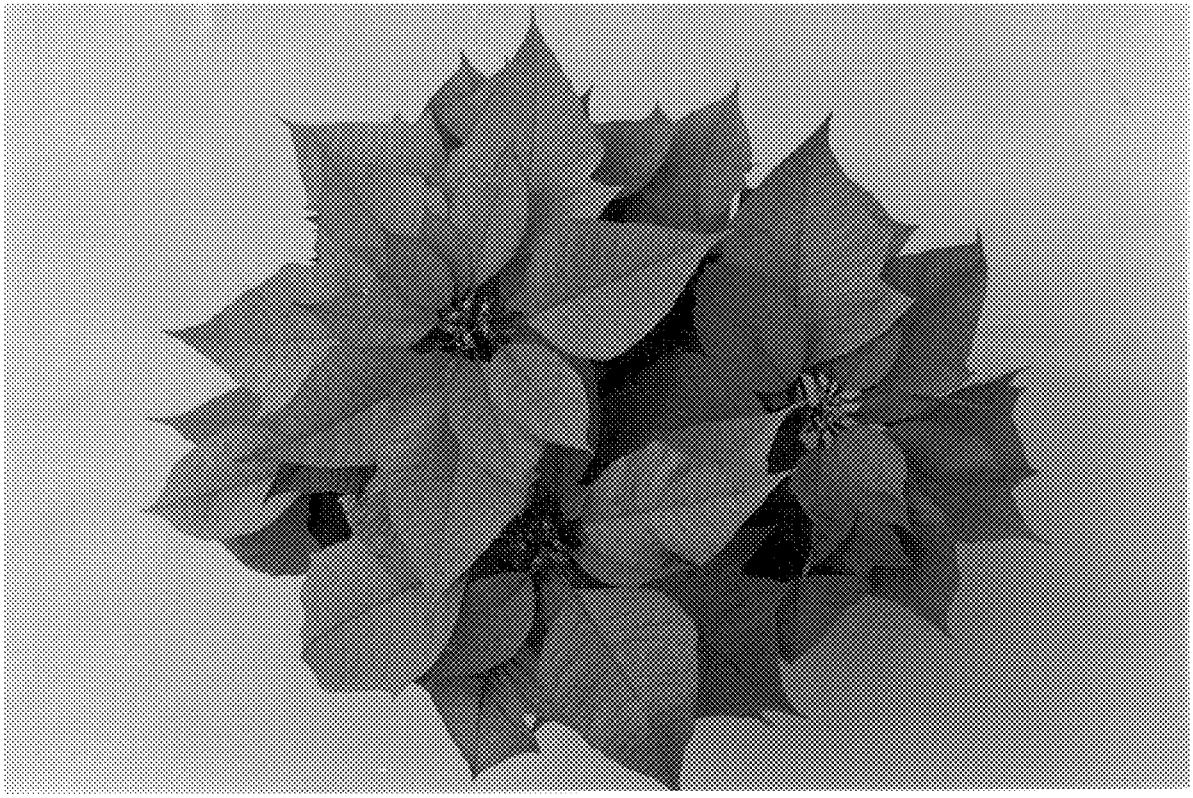
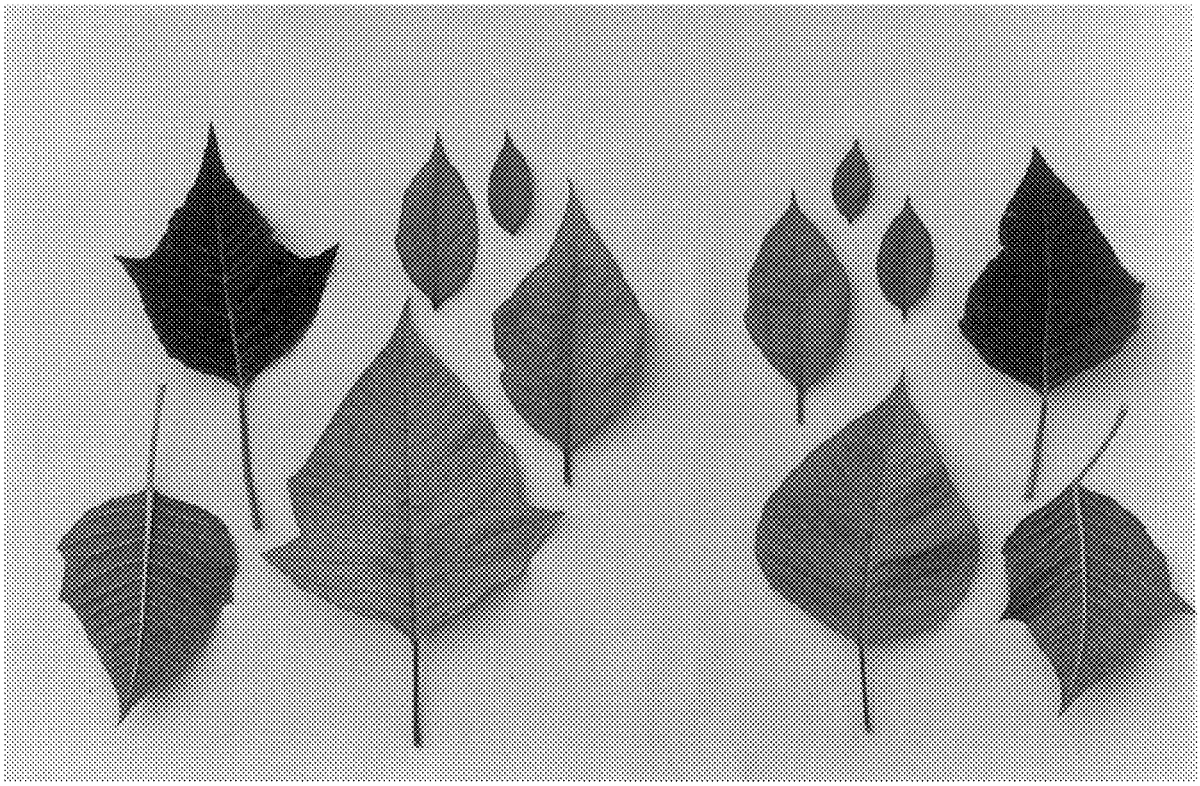

* * * * *